(12) United States Patent
Kang et al.

(10) Patent No.: US 8,867,701 B2
(45) Date of Patent: Oct. 21, 2014

(54) APPARATUS FOR CAPTURING RADIATION IMAGE, MEDICAL IMAGING SYSTEM, AND METHOD OF CAPTURING RADIATION IMAGE

(75) Inventors: Dong-goo Kang, Suwon-si (KR); Jong-chul Ye, Daejeon (KR); Ji-young Choi, Daejeon (KR); Young-hun Sung, Hwaseong-si (KR); Seok-min Han, Seongnam-si (KR)

(73) Assignees: Samsung Electronics Co., Ltd., Suwon-si (KR); Korea Advanced Institute of Science and Technology, Daejeon (KR)

( * ) Notice: Subject to any disclaimer, the term of this patent is extended or adjusted under 35 U.S.C. 154(b) by 342 days.

(21) Appl. No.: 13/465,012

(22) Filed: May 6, 2012

(65) Prior Publication Data

US 2012/0281810 A1    Nov. 8, 2012

(30) Foreign Application Priority Data

May 6, 2011   (KR) ........................ 10-2011-0043070

(51) Int. Cl.
*A61B 6/02*  (2006.01)
*A61B 6/00*  (2006.01)

(52) U.S. Cl.
CPC ................. *A61B 6/482* (2013.01); *A61B 6/583* (2013.01); *A61B 6/5217* (2013.01)
USPC .......................................................... 378/62

(58) Field of Classification Search
USPC ............................... 378/4, 5, 9, 62, 98.9, 207
See application file for complete search history.

(56) References Cited

U.S. PATENT DOCUMENTS

| | | | |
|---|---|---|---|
| 6,674,835 B2 | 1/2004 | Kaufhold et al. | |
| 6,683,934 B1 | 1/2004 | Zhao et al. | |
| 6,754,298 B2 * | 6/2004 | Fessler | 378/4 |
| 7,133,490 B2 * | 11/2006 | Muller et al. | 378/37 |
| 2002/0075997 A1 * | 6/2002 | Unger et al. | 378/98.9 |
| 2010/0301224 A1 | 12/2010 | Morel et al. | |

FOREIGN PATENT DOCUMENTS

JP    2010-530058 A    9/2010

* cited by examiner

*Primary Examiner* — Irakli Kiknadze

(57) ABSTRACT

An apparatus for capturing a radiation image of a subject including at least two materials includes a radiation irradiating unit configured to irradiate multi-energy radiation including at least two energy bands to a calibration model including a plurality of thicknesses of each of the at least two materials; an attenuation-coefficient estimating unit configured to estimate attenuation coefficients for each of the at least two materials for each of the at least two energy bands based on values obtained by passing the multi-energy radiation through the calibration model; and an energy-band determining unit configured to determine an optimal combination of at least two energy bands to be included in multi-energy radiation to be irradiated to the subject from a plurality of different combinations of at least two energy bands based on the estimated attenuation coefficients and the values obtained by passing the multi-energy radiation through the calibration model.

24 Claims, 6 Drawing Sheets

APPARATUS FOR CAPTURING RADIATION IMAGE, MEDICAL IMAGING SYSTEM, AND METHOD OF CAPTURING RADIATION IMAGE

CROSS-REFERENCE TO RELATED APPLICATIONS

This application claims the benefit of Korean Patent Application No. 10-2011-0043070 filed on May 6, 2011, in the Korean Intellectual Property Office, the disclosure of which is incorporated herein by reference in its entirety.

BACKGROUND

1. Field

This disclosure relates to apparatuses for capturing a radiation image, medical imaging systems, and methods of capturing a radiation image.

2. Description of the Related Art

A medical image system, which uses radiation, e.g., X-rays, obtains a projected radiation image by irradiating a subject, such as a human body, with the X-rays. According to the kind and density of the subject to be irradiated or energy band of the X-rays, an attenuation degree of the X-rays by a material is different. For instance, an attenuation coefficient of bone is very high in comparison with that of soft tissue. Accordingly, since the contrast between soft tissue and bone is high, the soft tissue and the bone are clearly distinguished from each other in the radiation image. However, different tissues included in the soft tissue have similar attenuation coefficients with respect to X-rays having a monochromatic energy band so that they also have similar intensities in the radiation image. Therefore, it is difficult to distinguish the different tissues included in the soft tissue in the radiation image.

SUMMARY

According to an aspect, an apparatus for capturing a radiation image of a subject that includes at least two materials includes a radiation irradiating unit configured to irradiate multi-energy radiation including at least two energy bands to a calibration model including a plurality of thicknesses of each of the at least two materials; an attenuation-coefficient estimating unit configured to estimate attenuation coefficients for each of the at least two materials for each of the at least two energy bands based on values obtained by passing the multi-energy radiation through the calibration model; and an energy-band determining unit configured to determine an optimal combination of at least two energy bands to be included in multi-energy radiation to be irradiated to the subject from a plurality of different combinations of at least two energy bands based on the attenuation coefficients estimated by the attenuation-coefficient estimating unit and the values obtained by passing the multi-energy radiation through the calibration model.

The energy-band determining unit may be further configured to determine the optimal combination of at least two energy bands to be included in the multi-energy radiation to be irradiated to the subject based on a condition number calculated based on an attenuation coefficient matrix and a photographing value matrix; the attenuation coefficient matrix may include the attenuation coefficients for each of the at least two materials for each of the at least two energy bands; and the photographing value matrix may include the values obtained by passing the multi-energy radiation through the calibration model.

The energy-band determining unit may be further configured to calculate the condition number based on a ratio of a maximum singular value and a minimum singular value of an estimation matrix calculated based on the attenuation coefficient matrix and the photographing value matrix.

The apparatus may further include an energy-band setting unit configured to set boundaries for dividing an energy band of radiation into at least two energy bands; and set a plurality of multi-energy radiations each including a different one of the plurality of different combinations of at least two energy bands by setting different boundaries for each of the plurality of multi-energy radiations.

The radiation irradiating unit may be further configured to irradiate the plurality of multi-energy radiations to the calibration model; the attenuation-coefficient estimating unit may be further configured to estimate respective attenuation coefficient matrixes for the plurality of multi-energy radiations based on values obtained by passing the multi-energy radiations through the calibration model; and the energy-band determining unit may be further configured to calculate estimation matrixes based on the attenuation coefficient matrixes and respective photographing value matrixes obtained by passing the multi-energy radiations through the calibration model; and determine a combination of at least two energy bands included in one of the multi-energy radiations as the optimal combination of at least two energy bands to be included in the multi-energy radiation to be irradiated to the subject based on a calculated estimation matrix having a minimum condition number among the calculated estimation matrixes.

The apparatus may further include a thickness estimating unit configured to estimate thicknesses of each of the at least two materials of the subject based on the attenuation coefficients and values obtained by passing the multi-energy radiation including the optimal combination of at least two energy bands through the subject.

The apparatus may further include a probability estimating unit configured to estimate probabilities that each pixel of the radiation image corresponds to each of the at least two materials of the subject based on the attenuation coefficients and values obtained by passing the multi-energy radiation including the optimal combination of at least two energy bands through the subject.

The probability estimating unit may be further configured to estimate the probabilities using an F-test method.

The apparatus may further include a diagnosis image generating unit configured to generate a diagnosis image showing probabilities that each pixel of the diagnosis image corresponds to one of the at least two materials of the subject based on the estimated probabilities.

The apparatus may further include a display unit for configured to display the diagnosis image.

The calibration model may include a plurality of calibration phantoms each including a different one of the plurality of thicknesses of a different one of the at least two materials; or a plurality of calibration phantoms each including the plurality of thicknesses of a different one of the at least two materials; or a single calibration phantom including the plurality of thicknesses of each of the at least two materials.

According to an aspect, a medical imaging system includes a radiation image capturing apparatus for capturing a radiation image of a subject that includes at least two materials. The radiation image capturing apparatus is configured to irradiate multi-energy radiation including at least two energy bands to a calibration model including a plurality of thicknesses of each of the at least two materials; estimate attenuation coefficients for each of the at least two materials for each of the at least two energy bands based on values obtained by passing the multi-energy radiation through the calibration model; determine an optimal combination of at least two energy bands to be included in multi-energy radiation to be irradiated to the subject from a plurality of different combinations of at least two energy bands based on the attenuation coefficients and the values obtained by passing the multi-energy radiation through the calibration model; and generate a diagnosis image of the subject by irradiating the multi-energy radiation including the optimal combination of at least two energy bands to the subject. The medical imaging system further includes a storage unit configure to store the diagnosis image; and an output unit configured to output the diagnosis image to an external device.

The radiation image capturing apparatus may be further configured to estimate probabilities that each pixel of the radiation image corresponds to each of the at least two materials of the subject based on the attenuation coefficients and values obtained by passing the multi-energy radiation including the optimal combination of at least two energy bands through the subject.

According to an aspect, a method of determining an optimal combination of at least two energy bands to be included in multi-energy radiation to be irradiated to a subject for capturing a radiation image of the subject, the subject including at least two materials, includes irradiating multi-energy radiation including at least two energy bands to a calibration model including a plurality of thicknesses of the at least two materials; estimating attenuation coefficients for each of the at least two materials for each of the at least two energy bands based on values obtained by passing the multi-energy radiation through the calibration model; and determining the optimal combination of at least two energy bands to be included in the multi-energy radiation to be irradiated to the subject from a plurality of different combinations of at least two energy bands based on the attenuation coefficients and the values obtained by passing the multi-energy radiation through the calibration model.

The determining may include determining the optimal combination of at least two energy bands to be included in the multi-energy radiation to be irradiated to the subject based on a condition number calculated based on an attenuation coefficient matrix and a photographing value matrix; the attenuation coefficient matrix may include the attenuation coefficients for each of the at least two materials for each of the at least two energy bands; and the photographing value matrix may include the values obtained by passing the multi-energy radiation through the calibration model.

The method may further include setting a plurality of multi-energy radiations each including a different one of the plurality of different combinations of at least two energy bands by setting different boundaries for dividing an energy band of radiation into at least two energy bands for each of the plurality of multi-energy radiations.

The method may further include irradiating the plurality of multi-energy radiations to the calibration model; estimating respective attenuation coefficient matrixes for the plurality of multi-energy radiations based on values obtained by passing the multi-energy radiations through the calibration model; calculating estimation matrixes based on the attenuation coefficient matrixes and respective photographing value matrixes obtained by passing the multi-energy radiations through the calibration models; and determining a combination of at least two energy bands included in one of the multi-energy radiations as the optimal combination of at least two energy bands to be included in the multi-energy radiation to be irradiated to the subject based on a calculated estimation matrix having a minimum condition number from the calculated estimation matrixes.

The method may further include irradiating the multi-energy radiation including the optimal combination of at least two energy bands to the subject; and estimating probabilities that each pixel of the radiation image corresponds to each of the at least two materials of the subject based on the attenuation coefficients and values obtained by passing the multi-energy radiation including the optimal combination of at least two energy bands through the subject.

According to an aspect, a non-transitory computer-readable storage medium stores a program for controlling a processor to perform the method of determining an optimal combination of at least two energy bands to be included in multi-energy radiation to be irradiated to a subject for capturing a radiation image of the subject described above.

According to an aspect, a method of processing a radiation image of a subject that includes at least two materials includes irradiating multi-energy radiation including at least two energy bands to a calibration model including a plurality of thicknesses of each of the at least two materials; estimating attenuation coefficients for each of the at least two materials for each of the at least two energy bands based on values obtained by passing the multi-energy radiation through the calibration model; irradiating the multi-energy radiation to the subject; and estimating probabilities that each pixel of the radiation image corresponds to each of the at least two materials of the subject based on the attenuation coefficients and values obtained by passing the multi-energy radiation through the subject.

According to an aspect, a non-transitory computer-readable storage medium stores a program for controlling a processor to perform the method of a method of processing a radiation image of a subject that includes at least two materials described above.

An apparatus for capturing a radiation image of a subject that the subject includes at least two materials includes an energy-band setting unit configured to set a plurality of different combinations of at least two energy bands; and set a plurality of multi-energy radiations each including a different one of the plurality of different combinations of at least two energy bands; a radiation irradiating unit configured to sequentially irradiate the plurality of multi-energy radiations to a calibration model including a plurality of thicknesses of each of the at least two materials of the subject so that the plurality of multi-energy radiations sequentially pass through the calibration model in a calibration operation; and irradiate a multi-energy radiation including an optimal combination of at least two energy bands to the subject so that the multi-energy radiation including the optimal combination of at least two energy bands passes through the subject in an imaging operation; an attenuation-coefficient estimating unit configured to acquire calibration measurement values of each of the plurality of multi-energy radiations after each of the multi-energy radiations has passed through the calibration model; and estimate attenuation coefficients for each of the at least two materials for each of the at least two energy bands of each of the plurality of multi-energy radiations based on the calibration measurement values; an energy-band determining unit configured to determine the optimal combination of at least two energy bands of the multi-energy radiation to be irradiated to the subject from the plurality of different combinations of at least two energy bands of the plurality of multi-energy radiations based on the estimated attenuation coefficients and the calibration measurement values; an image value estimating unit configured to acquire image measurement values of the multi-energy radiation including the optimal combination of at least two energy bands after the multi-energy radiation including the optimal combination of at least two energy bands has passed through the subject; and estimate image values indicative of the subject based on optimal estimated attenuation coefficients that correspond to the optimal combination of at least two energy bands among the estimated attenuation coefficients estimated by the attenuation-coefficient estimating unit and the image measurement values; and a diagnosis image generating unit configured to generate a diagnosis image of the subject based on the image values.

The image value estimating unit may include a thickness estimating unit configured to estimate, as the image values, thicknesses of each of the at least two materials of the subject based on the estimated optimal attenuation coefficients and the image measurement values; and the diagnosis image generating unit may be further configured to generate a diagnosis image of one of the at least two materials of the subject based on the estimated thicknesses.

The image value estimating unit may include a probability estimating unit configured to estimate, as the image values, probabilities that each pixel of the radiation image corresponds to each of the at least two materials of the subject based on the estimated optimal attenuation coefficients and the image measurement values; and the diagnosis image generating unit may be further configured to generate a diagnosis image including a plurality of pixels showing probabilities that each of the pixels corresponds to one of the at least two materials of the subject.

Additional aspects will be set forth in part in the description that follows and, in part, will be apparent from the description, or may be learned by practice of the described examples.

BRIEF DESCRIPTION OF THE DRAWINGS

The above and other aspects will become apparent and more readily appreciated from the following description of examples, taken in conjunction with the accompanying drawings of which.

DETAILED DESCRIPTION

Figure 1:
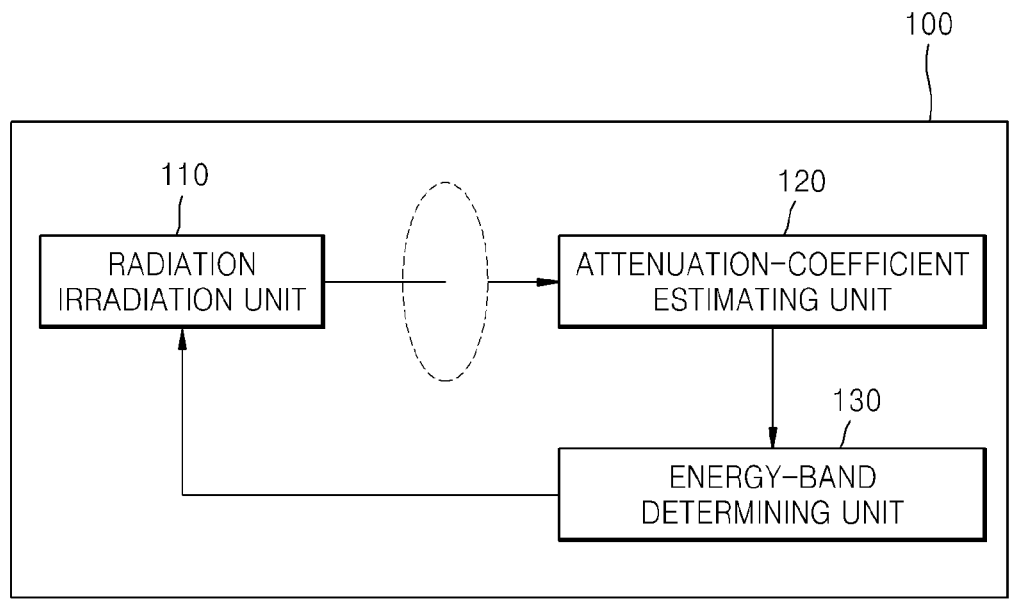
FIG. 1 is a block diagram of a radiation image capturing apparatus according to an example of the invention.

Reference will now be made in detail to examples of which are illustrated in the accompanying drawings, wherein like reference numerals refer to like elements throughout. In this regard, the examples may have different forms and should not be construed as being limited to the descriptions set forth herein. Accordingly, the examples are merely described below, by referring to the figures, to explain aspects of the description.

FIG. 1 is a block diagram of a radiation image capturing apparatus 100 according to an example of the invention. Referring to FIG. 1, the radiation image capturing apparatus 100 includes a radiation irradiating unit 110, an attenuation-coefficient estimating unit 120, and an energy-band determining unit 130.

Elements related to this example are illustrated in FIG. 1. However, it will be understood by those skilled in the art that besides the elements illustrated in FIG. 1, other general elements may be further included.

The attenuation-coefficient estimating unit 120 and the energy-band determining unit 130 of the radiation image capturing apparatus 100 may correspond to a single processor or a plurality of processors. The processor may be embodied with an array of a plurality of logic gates, or may be embodied with a combination of a general microprocessor and a memory where a program to be run in the microprocessor is stored. It will be also understood by those skilled in the art that the attenuation-coefficient estimating unit 120 and the energy-band determining unit 130 may be embodied with another form of hardware.

The radiation image capturing apparatus 100 captures a radiation image of a subject including at least two materials. In this case, radiation may include X-rays, and thus the radiation image capturing apparatus 100 may be an image capturing apparatus for mammography that is used to detect a lesion of breast tissue including soft tissue only, other than a bone, but is not limited thereto.

The radiation irradiation unit 110 irradiates multi-energy radiation having at least two energy bands to a calibration model that is formed of at least two materials with each of the at least two materials having a plurality of thicknesses. In this case, the at least two materials are the same as the at least two materials included in the subject.

The subject according to the this example includes at least two materials. For example, the subject may be a human breast, abdomen, heart, bone, or the like. When the subject is the human breast, the at least two materials may include adipose tissue, glandular tissues, microcalcifications, carcinoma tissues, and the like.

The calibration model that is formed of at least two materials with each of at least two materials having a plurality of thicknesses may be a calibration phantom. Calibration phantoms per se are well known in the art, and thus will not be described in detail here.

More specifically, the calibration model according to this example may correspond to a plurality of calibration phantoms formed of a single material with a single thickness, or a plurality of calibration phantoms formed of a single material with a plurality of thicknesses, or a single calibration phantom formed of a plurality of materials with each of materials having a plurality of thicknesses.

For example, a plurality of calibration phantoms having a block shape may be formed of a single material with thicknesses of 1 cm, 2 cm, 3 cm, 4 cm, and 5 cm, and may be provided with respect to a plurality of materials in a similar manner. However, the calibration model is not limited to this, but can be provided in any manner that provides a plurality of materials each having a plurality of thicknesses.

The calibration model according to this example has substantially the same structure as the subject; however, calibration model is not limited to this.

Hereinafter in the detailed description, the calibration model will be referred to as "calibration means," and the term "calibration means" is to be construed to mean "calibration model."

The radiation irradiation unit 110 irradiates multi-energy radiation having at least two energy bands. If the multi-energy radiation is an X-ray, the radiation irradiation unit 110 forms an X-ray source spectra including combinations of at least two energy bands, generates the multi-energy radiation including combinations of at least two energy bands, and irradiates the generated multi-energy radiation to the calibration means.

The radiation irradiation unit 110 irradiates the multi-energy radiation including combinations of energy bands determined by the energy-band determining unit 130 to the subject. Thus, the radiation irradiation unit 110 irradiates the multi-energy radiation including optimized combinations of energy bands so as to reduce noise of a radiation image captured by the radiation image capturing apparatus 100, thereby improving a quality of the radiation image.

The attenuation-coefficient estimating unit 120 estimates attenuation coefficients of each of the at least two materials with respect to each of the at least two energy bands by using values obtained when the multi-energy radiation irradiated by the radiation irradiation unit 110 passes through the calibration means.

If radiation with different energy bands is irradiated to a single tissue, an amount of radiation absorbed into the tissue may vary according to an energy band of the irradiated radiation. Based on this characteristic, the attenuation-coefficient estimating unit 120 acquires a plurality of radiation images in which attenuation characteristics for respective energy bands are reflected, and estimates the attenuation coefficients by using the acquired radiation images.

For example, when monochromatic energy radiations corresponding to the respective at least two energy bands are irradiated to the calibration means, the attenuation-coefficient estimating unit 120 acquires a plurality of radiation images in which attenuation characteristics for respective energy bands are reflected, and estimates attenuation coefficients by using the acquired radiation images.

As another example, when multi-energy radiation having at least two energy bands is irradiated to the calibration means, the attenuation-coefficient estimating unit 120 acquires a plurality of radiation images in which attenuation characteristics for the respective energy bands are reflected by using an energy discrimination detector, and estimates attenuation coefficients by using the acquired radiation images. In this case, the energy discrimination detector may be a photon counting detector, but is not limited thereto.

The attenuation-coefficient estimating unit 120 estimates attenuation coefficients of each of the at least two materials with respect to each of the at least two energy bands by using values obtained by passing the multi-energy radiation through the calibration means, which will now be described in greater detail.

A photographing value and a measurement value may be given by the following Equations 1 and 2, and are obtained when radiation with an i-th energy band from among M energy bands is passing through a calibration means including K materials.

$$\lambda_i = \sum_{j \in N_i} I_{oj} \cdot \exp\left(-\sum_{k=1}^{K} \mu_{kj} t_k\right), \quad (1)$$

$$N_i = \{j \mid l_i \le Energy_j \le u_i\}$$

$$y_i = \ln \lambda_i \quad (2)$$

In Equations 1 and 2, i is an index for an energy band of photographed measurement value, j is an index for monochromatic energy included in an energy band from among M energy bands, $\lambda_i$ is a photographing value for the i-th energy band, $I_{oj}$ is an intensity of incident radiation of the i-th energy band, $l_i$ is a lower boundary of the i-th energy band, $u_i$ is an upper boundary of the i-th energy band, $Energy_j$ is a j-th monochromatic energy, $\mu_{kj}$ is an attenuation coefficient of a k-th material with respect to the j-th monochromatic energy, $t_k$ is a thickness of the k-th material, and $y_i$ is a measurement value with respect to the i-th energy band. In addition, units of $l_i$, $u_i$ and $Energy_j$ may be keV, but are not limited thereto.

In this case, Equation 1 is defined according to the Beer-Lambert Law. Thus, the photographing value $\lambda_i$ is an ideal value, and thus the attenuation-coefficient estimating unit 120 may acquire the measurement value $y_i$.

A radiation image of the calibration means may be indicated by using the photographing value $\lambda_i$ or the measurement value $y_i$.

Thus, when the radiation irradiation unit 110 irradiates multi-energy radiation having M energy bands to the calibration means including K materials, measurement values with respect to respective energy bands, which are acquired by the attenuation-coefficient estimating unit 120, may be given in a matrix form as shown in the following Equation 3.

$$\begin{bmatrix} y_1 \\ \vdots \\ y_M \end{bmatrix} = \begin{bmatrix} \mu_1(E_1) & \cdots & \mu_k(E_1) \\ \vdots & \ddots & \vdots \\ \mu_1(E_M) & \cdots & \mu_K(E_M) \end{bmatrix} \begin{bmatrix} t_1 \\ \vdots \\ t_K \end{bmatrix} + \begin{bmatrix} b_1 \\ \vdots \\ b_M \end{bmatrix} \rightarrow y = At + b \quad (3)$$

In Equation 3, $y_m$ is a measurement value when radiation with a m-th energy band is irradiated, $\mu_k(E_m)$ is a representative attenuation coefficient when radiation with the m-th energy band is irradiated to a k-th material, $t_k$ is a thickness of a k-th material, and $b_m$ is an offset value when radiation with the m-th energy band is irradiated.

Thus, Equation 3 may be defined by y=At+b, where y is a measurement value matrix, A is an attenuation coefficient matrix, t is a material thickness matrix, and b is a offset value matrix.

In this case, b corresponding to the offset value matrix may be a background value. For example, when t=0 in y=At+b, the measurement value y=b. That is, a measurement value when radiation is not passing through any material corresponds to an offset value. Thus, the offset value matrix b may be given by the following Equation 4.

$$b = E(y_{bg}) \quad (4)$$

In Equation 4, $y_{bg}$ is a measurement value when t=0, and $E(y_{bg})$ is an average pixel value of pixels forming a radiation image indicating a background.

In order for the attenuation-coefficient estimating unit 120 to estimate an attenuation coefficient, the calibration means has the same structure as the subject. Thus, when the calibration means is configured so that K materials have B thicknesses, respectively, a measurement value of the calibration means including a k-th material having a b-th thickness may be given by the following Equation 5.

$$[y^{11} \ y^{21} \ \ldots \ y^{KB}] - b = A \begin{bmatrix} l_1 & 0 & \ldots & 0 & l_2 & 0 & \ldots & 0 & 0 \\ 0 & l_1 & & \vdots & 0 & l_2 & & \vdots & \ldots & \vdots \\ \vdots & & \ddots & 0 & \vdots & & \ddots & 0 & 0 \\ 0 & \ldots & 0 & l_1 & 0 & \ldots & 0 & l_2 & l_B \end{bmatrix} \quad (5)$$

In Equation 5, $y^{kb}$ is a measurement value a k-th material having a b-th thickness of the calibration means, b is an offset value matrix, A is an attenuation coefficient matrix, and $l_b$ is a thickness of a b-th thickness of the calibration means.

The following Equation 6 may be defined by organizing Equation 5 by using the Kronecker product.

$$y - b = A(t^T \otimes I_K), t = \begin{bmatrix} l_1 \\ \vdots \\ l_B \end{bmatrix} \quad (6)$$

In Equation 6, y is a measurement value matrix, b is an offset value matrix, A is an attenuation coefficient matrix, t is a calibration means thickness matrix including $l_1$ through $l_B$, $I_K$ is an identify matrix having a size of K×K, and $\otimes$ is a notation defined according to the Kronecker product.

The following Equations 7 and 8 may be defined by organizing Equation 6.

$$(y-b)^T = (t \otimes I_K) A^T \quad (7)$$

$$A = ((t \otimes I_K)^+ (y-b)^T)^T \quad (8)$$

In Equations 7 and 8, y is a measurement value matrix, b is a offset value matrix, A is an attenuation coefficient matrix, t is a calibration means thickness matrix including $l_1$ through $l_B$, $I_K$ is an identity matrix having a size of K×K, $\otimes$ is a notation defined according to the Kronecker product, and $(\cdot)^+$ is a notation indicating a pseudoinverse.

In addition, in Equation 8, in order to reduce a computational amount, a pseudoinverse is calculated according to a least squares method. However, this example is not limited to this, and the attenuation-coefficient estimating unit 120 may calculate an inverse matrix.

Thus, according to this example, the attenuation-coefficient estimating unit 120 estimates the attenuation coefficient matrix A by using y that is obtained by passing multi-energy radiation emitted from the radiation irradiation unit 110 through the calibration means.

In this case, the attenuation coefficient matrix A includes attenuation coefficients of each of a plurality of materials included in the calibration means with respect to respective energy bands included in the multi-energy radiation emitted from the radiation irradiation unit 110. In addition, a value obtained by passing multi-energy radiation through the calibration means includes the measurement value matrix y and the offset value matrix b.

Thus, the attenuation-coefficient estimating unit 120 estimates an attenuation coefficient by using the calibration means having the same structure as the subject.

The energy-band determining unit 130 determines an optimal combination from among combinations of at least two energy bands to be included in multi-energy radiation having at least two energy bands with reference to the attenuation coefficient estimated by the attenuation-coefficient estimating unit 120 and the value obtained by passing multi-energy radiation through the calibration means.

For example, the energy-band determining unit 130 determines an optimal combination from among combinations of at least two energy bands to be included in multi-energy radiation with reference to a condition number of an estimation matrix calculated by using an attenuation coefficient matrix and a photographing value matrix. In this case, the attenuation coefficient matrix may include attenuation coefficients of each of at least two materials with respect to respective at least two energy bands, and the photographing value matrix may include photographing values obtained by passing multi-energy radiation having at least two energy bands through the calibration means. For example, the photographing value matrix may be a diagonal matrix including photographing values.

The energy-band determining unit 130 may calculate a condition number by using a ratio of a maximum singular value and a minimum singular value of the estimation matrix calculated by using the attenuation coefficient matrix and the photographing value matrix.

Since the energy-band determining unit 130 determines an optimal combination with respect to at least two energy bands to be included in multi-energy radiation with reference to the condition number of the estimation matrix, the radiation image capturing apparatus 100 may correctly estimate thicknesses of at least two materials included in the subject.

Hereinafter, it will be described that the condition number of the estimation matrix is used as an important factor for correctly estimating thicknesses of at least two materials included in the subject.

It will be understood by those skilled in the art that photographing values with respect to respective energy bands follow a Poisson distribution as multi-energy radiation is irradiated.

In addition, if it is assumed that photographing values $d_i$ with respect to an i-th energy band from among energy bands included in multi-energy radiation follow a Poisson distribution with an average $\lambda_i$ and a variance $\lambda_i$, photographing values $d_i$ with respect to respective energy bands independently follow a Poisson distribution. In this case, $\lambda_i$ may be an ideal photographing value, and $d_i$ may be an actual photographing value.

Thus, a probability distribution of all photographing values obtained by passing multi-energy radiation having M energy bands through the calibration means may be given by the following Equation 9.

$$f(d \mid t) = \prod_{i=1}^{M} f(d_i \mid t) = \prod_{i=1}^{M} \frac{\lambda_i^{d_i}}{d_i!} \exp(-\lambda_i) \quad (9)$$

In Equation 9, d is all photographing values when multi-energy radiation is irradiated to the calibration means, t is a thickness of a material included in the calibration means, $d_i$ is an actual photographing value when radiation of an i-th energy band is irradiated, and $\lambda_i$ is an ideal photographing value when the i-th energy band is irradiated. In addition, $\lambda_i$ may be defined by Equation 1.

A log-likelihood of a Poisson distribution according to Equation 9 may be according to the following Equation 10 as being approximated in a form of a weighted l-2 norm.

$$\ln f(d \mid t) = \sum_{i=1}^{M} (d_i \ln \lambda_i - \lambda_i - \ln d_i!) \quad (10)$$

The following Equation 12 is defined by organizing Equation 10 by setting a condition given by the following Equation 11.

$$-\ln \lambda_i \approx A_i t + b_i \quad (11)$$
$$P_i \equiv A_i t$$

$$\ln f(d \mid t) \approx \sum_{i=1}^{M} (-d_i(p_i + b_i) - \exp(-p_i - b_i) - \ln d_i!) \quad (12)$$

In Equations 11 and 12, $A_i$ is an attenuation coefficient matrix with respect to an i-th energy band, and t is a calibration means thickness matrix.

The following Equation 13 may be defined by approximating $p_i$ of Equations 11 and 12. The following Equation 14 may be defined by applying a second-order Taylor series approximation to the approximated $p_i$.

$$\hat{p}_i = -\log d_i - b_i \quad (13)$$

$$\ln f(d \mid t) \approx \sum_{i=1}^{M} \left( d_i \log d_i - d_i - \ln d_i! - \frac{1}{2} d_i (p_i + \hat{p}_i)^2 \right) \quad (14)$$

A matrix form such as the following Equation 16 may be defined by organizing Equation 14 by setting a condition given by the following Equation 15.

$$y_i = -\log d_i \quad (15)$$

$$\ln f(d \mid t) \approx -\tfrac{1}{2}(y - At - b)^T D(y - At - b) + c(d) \quad (16)$$

In Equation 16, d is a vector including photographing values $d_i$ when radiation of an i-th energy band is irradiated, and D is a diagonal matrix including photographing values $d_i$ as diagonal values when radiation of an i-th energy band is irradiated.

A Poisson probability distribution f(d|t) may be approximated by using a Gaussian distribution including an average (At+b) and a covariance matrix D. Thus, f(d|t) is given by the following Equation 17 in that independent two functions are multiplied.

$$\begin{aligned} f(d \mid t) &\approx \exp\left(-\frac{1}{2}(y - At - b)^T D(y - At - b) + c(d)\right) \\ &= \exp\left(-\frac{1}{2}(y - b)^T D(y - b) + c(d)\right) \exp\left(-\frac{1}{2}(At)^T D(At)\right) \\ &\quad \exp((At)^T D(y - b)). \end{aligned} \quad (17)$$

The independent two functions defined in Equation 17 may be defined by the following Equation 18.

$$h(d) = \exp(-\tfrac{1}{2}(y-b)^T D(y-b) + c(d))$$

$$g(T(d) \mid t) = \exp(-\tfrac{1}{2}(At)^T D(At)) \exp((At)^T D(\ln d - b)) \quad (18)$$

Sufficient statistics T(d) with respect to t may be given by the following Equation 19, with reference to g(T(d)|t) defined in Equation 18.

$$T(d) = A^T D(\ln d - b) \quad (19)$$

As defined in Equation 19, a sufficient statistic with respect to a thickness t of a material included in the calibration means may be calculated by using the attenuation coefficient matrix A, the photographing value d, the diagonal matrix D including photographing values d, and the offset value b.

A correct distribution of random variances may be obtained when sufficient statistics with respect to random variances are known. Thus, a distribution of the thickness t of the material included in the calibration means may be estimated according to the sufficient statistic calculated by using Equation 19.

When sufficient statistics T(d) and an unbiased estimator t' with respect to a thickness t of a material included in the calibration means are given, an expectation value E(t'|T(d)) has a smaller variance than the unbiased estimator t' according to the Rao-Blackwell-Lehmann-Scheffé theorem. In addition, since the sufficient statistics T(d) has a completeness characteristic, the unbiased function including T(d) may be a minimum variance unbiased estimator with respect to t.

Based on this theorem, the unbiased estimator t' of t may be given by the following Equation 21 by using t for minimizing a cost function of the following Equation 20 from the log-likelihood of f(d|t) of Equation 16.

$$t' = \min_t (y - At - b)^T D(y - At - b) \quad (20)$$

$$t' = (A^T D A)^{-1} A^T D(y - b) \quad (21)$$

Thus, the expectation value E(t'|T(d)) may be given by the following Equation 22.

$$\begin{aligned} E(t' \mid T(d)) &= (A^T D A)^{-1} A^T D E(y - b) \\ &= (A^T D A)^{-1} A^T D A t = t \end{aligned} \quad (22)$$

As described above, since T(d) has a completeness characteristic according to a Gaussian distribution, the unbiased estimator t' is a minimum variance unbiased estimator of t. When an estimation matrix $\tilde{A}$ is defined by the following Equation 23, it may be known that a condition number of the estimation $\tilde{A}$ is important to estimate a thickness t of a material from a minimum variance unbiased estimator $(A^T D A)^{-1} A^T D(y-b)$ of t according to Equation 21.

$$\tilde{A} = D^{1/2} A \quad (23)$$

In Equation 23, A is an attenuation coefficient matrix, and D is a photographing value matrix. For example, the photographing value matrix may be a diagonal matrix including photographing values.

Thus, the energy-band determining unit 130 determines an optimal combination with respect to at least two energy bands to be included in multi-energy radiation, with reference to a condition number of the estimation matrix $\tilde{A}$.

Hereinafter, a method of calculating a condition number of the estimation matrix $\tilde{A}$ in the energy-band determining unit 130 will be described. The condition number of the estimation matrix $\tilde{A}$ may indicate a ratio of a maximum singular value and a minimum singular value of an estimation matrix.

In detail, the condition number of the estimation matrix $\tilde{A}$ indicates a limit of a variance by which a variance of a measurement value y affects a thickness t of a material included in the calibration means. Thus, the variance of the thickness t of the material included in the calibration means may be defined by the following Equation 24.

$$\Delta t = \tilde{A}^+ D^{1/2} \cdot \Delta y \quad (24)$$

In Equation 24, $\tilde{A}^+$ is a pseudo inverse of the estimation matrix $\tilde{A}$. That is, since the pseudo inverse $A^+$ of $A$ may be defined by $(A^T A)^{-1} A^T$, Equation 24 about a variance of t is defined from Equation 21.

In addition, a condition such as the following Equation 25 may be satisfied from Equation 24 according to definition of the condition number.

$$\|\Delta t\| \leq \|\tilde{A}^+\|_s \|D^{1/2} \cdot \Delta y\| \quad (25)$$

In Equation 25, $\|\cdot\|_s$ notation is a spectral norm. For example, when $y = Fx$, a condition such as $\|y\| \leq \|F\| \|x\|$ is satisfied. In this case, the condition such as $\|y\| \leq \|F\| \|x\|$ may be obtained from a relationship such as $\|Fx\| \leq f_{sv} \|x\|$ (where $f_{sv}$ is a maximum singular value of F). $\|Fx\| \leq f_{sv} \|x\|$ may be obtained from a relationship such as $\max\|Fx\|/\|x\| = f_{sv}$ (where $f_{sv}$ is a spectral norm of a matrix F).

As described above, Equation 25 may be obtained from Equation 24. Thus, an upper limit of a norm of a variance of t may be given by Equation 25.

In addition, since a spectral norm of a matrix is expressed by a maximum singular value of the matrix, a spectral norm of the pseudo inverse $\tilde{A}^+$ of an estimation matrix may be defined by the following Equation 26.

$$\|\tilde{A}^+\|_s = \frac{1}{\sigma_n} \quad (26)$$

In Equation 26, $\sigma_n$ is a minimum singular value from among singular values of the estimation matrix $\tilde{A}$.

In Equations 21 and 23, it may be known that a product of the estimation matrix $\tilde{A}$ and a material thickness t is the same as $D^{1/2}(y-b)$. According to the definition of the condition number as defined in Equation 25, a lower limit of a norm of t may be defined by the following Equation 27.

$$\|t\| \geq \frac{\|D^{\frac{1}{2}}(y-b)\|}{\|\tilde{A}\|_s} \quad (27)$$

In Equation 27, the spectral norm of the estimation matrix $\tilde{A}$ may be a maximum singular value from among singular values of the estimation matrix $\tilde{A}$. Thus, when the maximum singular value from among the singular values of the estimation matrix $\tilde{A}$ is $\sigma_1$, and a minimum singular value from among the singular values of the estimation matrix $\tilde{A}$ is $\sigma_n$, a boundary of a ratio of t and a variance of t may be given by the following Equation 28.

$$\frac{\|\Delta t\|}{\|t\|} \leq \frac{\sigma_1}{\sigma_n} \frac{\|D^{\frac{1}{2}} y\|}{\|D^{\frac{1}{2}}(y-b)\|} \quad (28)$$

Thus, as defined in Equation 28, the condition number of the estimation matrix $\tilde{A}$ may be given by the following Equation 29.

$$K(\tilde{A}) \equiv \frac{\sigma_1}{\sigma_n} \quad (29)$$

In Equation 29, $K(\tilde{A})$ is the condition number of the estimation matrix $\tilde{A}$.

Thus, the energy-band determining unit 130 calculates the condition number of the estimation matrix $\tilde{A}$ by using a ratio of the maximum singular value and the minimum singular value of the estimation matrix $\tilde{A}$, as defined in Equation 29, and determines combinations of at least two energy bands to be included in multi-energy radiation with reference to the calculated condition number.

Thus, the radiation image capturing apparatus 100 determines combinations of at least two energy levels to be included in multi-energy radiation with reference to the attenuation coefficient and the photographing value so as to reduce noise of a radiation image captured by the radiation image capturing apparatus 100, thereby correctly estimating thicknesses of materials included in the subject.

Figure 2:
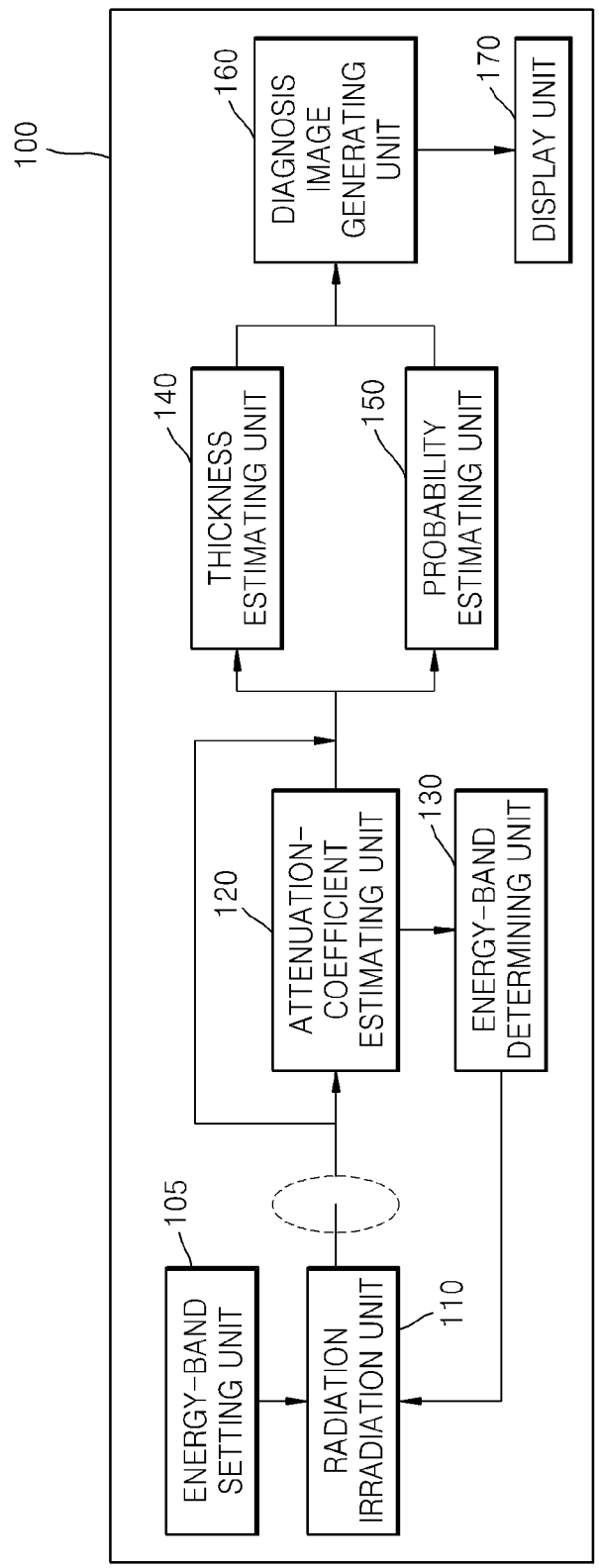
FIG. 2 is a detailed block diagram of a radiation image capturing apparatus according to an example of the invention.

FIG. 2 is a detailed block diagram of the radiation image capturing apparatus 100 according to an example of the invention. Referring to FIG. 2, the radiation image capturing apparatus 100 includes an energy-band setting unit 105, the radiation irradiation unit 110, the attenuation-coefficient estimating unit 120, the energy-band determining unit 130, a thickness estimating unit 140, a probability estimating unit 150, a diagnosis image generating unit 160, and a display unit 170.

Elements related to this example are illustrated in FIG. 2. However, it will be understood by those skilled in the art that besides the elements illustrated in FIG. 2 other general elements may be further included.

The radiation image capturing apparatus 100 of FIG. 2 corresponds to an example of the radiation image capturing apparatus 100 of FIG. 1. Thus, units of the radiation image capturing apparatus 100 are not limited to units illustrated in FIG. 2. The detailed description of the radiation image capturing apparatus 100 of FIG. 1 is also applicable to the radiation image capturing apparatus 100 of FIG. 2, and thus is not repeated herein. The energy-band setting unit 105, the attenuation-coefficient estimating unit 120, the energy-band determining unit 130, the thickness estimating unit 140, the probability estimating unit 150, and the diagnosis image generating unit 160 of the radiation image capturing apparatus 100 of FIG. 2 may correspond to a single processor or a plurality of processors.

The radiation image capturing apparatus 100 captures a radiation image of a subject including at least two materials.

The energy-band setting unit 105 sets boundaries for dividing an energy band of radiation into at least two energy bands, and sets a plurality of multi-energy radiations having different combinations of at least two energy bands. For example, the energy band corresponding to radiation may be 10 keV or more, or 49 keV or less, but is not limited thereto.

Hereinafter, for convenience of description, a case where multi-energy radiation includes combinations of three energy bands including first through third energy bands will be described, but this example is not limited thereto.

The energy-band setting unit 105 sets boundaries for dividing the energy band corresponding to radiation into three energy bands. In this case, the energy-band setting unit 105 may set the boundaries by using an interval of 1 keV, but this example is not limited thereto.

For example, the energy-band setting unit 105 may set boundaries for dividing the energy band corresponding to radiation into at least three energy bands to be 11 keV and 12 keV. In this case, a range of first energy band included in multi-energy radiation may be 10 keV or more, or 11 keV or less. A range of second energy band included in multi-energy radiation may be 11 keV or more, or 12 keV or less. A range of third energy band included in multi-energy radiation may be 12 keV or more, or 49 keV or less.

By using the above-described method, the energy-band setting unit 105 may set two boundaries within a range of 10 keV to 49 keV so as to set multi-energy radiation including various combinations having three energy bands, which will be described later in detail with reference to FIG. 3.

The radiation irradiation unit 110 irradiates multi-energy radiation having at least two energy bands to any one of a calibration means which includes at least two materials with each of at least two materials having a plurality of thicknesses and a subject. In this case, the radiation irradiation unit 110 may irradiate a plurality of multi-energy radiations set by the energy-band setting unit 105.

The attenuation-coefficient estimating unit 120 may estimate attenuation coefficients of each of at least two materials with respect to respectively at least two energy bands by using values obtained by passing multi-energy radiation through the calibration means. In this case, the estimated attenuation coefficients may correspond to an attenuation coefficient matrix including attenuation coefficients of each of at least two materials with respect to each of at least two energy bands.

In addition, the attenuation-coefficient estimating unit 120 estimates attenuation coefficient matrixes for the respective multi-energy radiations set by the energy-band setting unit 105 by using the values obtained by passing multi-energy radiation through the calibration means.

The energy-band determining unit 130 determines an optimal combination from among combinations of at least two energy bands to be included in multi-energy radiation by using the attenuation coefficients estimated by the attenuation-coefficient estimating unit 120.

For example, the energy-band determining unit 130 calculates estimation matrixes by using the attenuation coefficient matrixes and photographing value matrixes, and determines a combination of at least two energy bands included in multi-energy radiation as an optimal combination of multi-energy radiation, according to an estimation matrix having a minimum condition number from among the calculated estimation matrixes. In this case, a condition number of an estimation matrix may be calculated by using a ratio of a maximum singular value and a minimum singular value.

The thickness estimating unit 140 estimates thicknesses of each of at least two materials included in the subject by using the attenuation coefficients estimated by the attenuation-coefficient estimating unit 120 and values obtained by irradiating multi-energy radiation having the combination of at least two energy bands determined by the energy-band determining unit 130 to the subject.

Referring to Equation 8, the thickness of each material included in the subject may be restored according to the following Equation 30 by using an attenuation coefficient matrix and an offset value matrix.

$$t = A^+(y - b) \tag{30}$$

In Equation 30, t is a material thickness matrix, A is an attenuation coefficient matrix, $(\cdot)^+$ is a notation indicating a pseudoinverse, y is a matrix including measurement values of the subject, and b is an offset value matrix.

Thus, the thickness estimating unit 140 may estimate thicknesses of a plurality of materials included in the subject by using the attenuation coefficients and the measurement values of the subject.

Hereinafter, a method of obtaining Equation 30 will be described. Since the radiation image capturing apparatus 100 uses a paddle, the radiation image capturing apparatus 100 may recognize an entire thickness of the subject through which radiation passes. Thus, thicknesses of materials may be estimated by using bases of which number is smaller by one than the number of materials included in the subject. Thus, the thickness estimating unit 140 may correctly estimate the thicknesses of the materials.

Hereinafter, a case where the subject includes first through third materials, but this example is not limited thereto. When an entire thickness of the subject is T, and thicknesses of the first through third materials are $t_a$, $t_b$, and $t_c$, the following Equation 31 may be satisfied.

$$T = t_a + t_b + t_c \tag{31}$$

Since respective columns of an attenuation coefficient matrix A correspond to first through third materials, the attenuation coefficient matrix may be defined by the following Equation 32.

$$A = [a_b a_c a_a] \tag{32}$$

In Equation 32, $a_a$ is a column including attenuation coefficients of the first material, $a_b$ is a column including attenuation coefficients of the second material, and $a_c$ is a column including attenuation coefficients of the third material.

Referring to Equations 3 and 32, an attenuation coefficient and a value obtained by irradiating multi-energy radiation to the subject may be defined by the following Equation 33.

$$\begin{aligned} y &= [a_b \quad a_c \quad a_a] \begin{bmatrix} t_b \\ t_c \\ t_a \end{bmatrix} + b \\ &= [a_b \quad a_c \quad a_a] \begin{bmatrix} T - t_c - t_a \\ t_c \\ t_a \end{bmatrix} + b \\ &= [a_c - a_b \quad a_a - a_b \quad a_b T + b] \begin{bmatrix} t_c \\ t_a \\ 1 \end{bmatrix} \end{aligned} \tag{33}$$

In Equation 33, y is a matrix including measurement values of the subject, T is an entire thickness of the subject, $t_a$, $t_b$, and $t_c$ are respective thicknesses of the first through third materials included in the subject, and $a_a$, $a_b$, and $a_c$ are respective attenuation coefficients of the first through third materials included in the subject.

Thus, thicknesses of materials, which are estimated by the thickness estimating unit 140, may be defined by the following Equation 34.

$$\begin{bmatrix} t_c \\ t_a \end{bmatrix} = [a_c - a_b \quad a_a - a_b]^+ [y - a_b T - b], \tag{34}$$

$$t_b = T - t_c - t_a$$

Thus, the thickness estimating unit 140 may estimate thicknesses of a plurality of materials included in the subject according to Equation 34. Equation 34 has the same meaning as Equation 30.

The thickness estimating unit 140 estimates a thickness of a material by using linear approximation, like in Equations 33 and 34. However, this example is not limited to this, and the thickness estimating unit 140 may estimate a thickness of a material by using nonlinear approximation.

When nonlinear approximation is performed on a third material c from among materials included in the subject, the following Equation 35 is defined by organizing Equation 3.

$$y = A_2 t + c t_c^2 + b \tag{35}$$

In Equation 35, y is a matrix including measurement values of the subject, $A_2$ is an attenuation coefficient matrix, c is an attenuation coefficient matrix of the third material, t is a matrix including thicknesses of the materials, $t_c$ is a matrix including thicknesses of the third material, and b is an offset value matrix.

Thus, with reference to Equation 35 and Equation 5 according to linear approximation, when nonlinear approximation is performed on the third material from among the materials included in the subject, the following Equation 36 may be defined by organizing Equation 5.

$$[y^{11} \quad y^{21} \quad \ldots \quad y^{KB}] - b = \qquad (36)$$

$$[A|c]\begin{bmatrix} l_1 & 0 & \ldots & 0 & l_2 & 0 & \ldots & 0 & 0 \\ 0 & l_1 & & \vdots & 0 & l_2 & & \vdots & \vdots \\ \vdots & & \ddots & 0 & \vdots & & \ddots & 0 & \ldots & 0 \\ 0 & \ldots & 0 & l_1 & 0 & \ldots & 0 & l_2 & l_B \\ 0 & l_1^2 & \ldots & 0 & 0 & l_2^2 & \ldots & 0 & 0 \end{bmatrix}$$

In addition, when an entire thickness of the materials is known, the following Equation 37 may be defined by organizing Equation 36, like in Equation 33.

$$y - b - a_b T = [a_c - a_b \quad a_a - a_b \quad c] \begin{bmatrix} t_c \\ t_a \\ t_c^2 \end{bmatrix} \qquad (37)$$

The thickness estimating unit 140 may use a method defined in Equation 38 or Equation 39 discussed below in order to estimate thicknesses of materials included in the subject by using Equation 37.

The thickness estimating unit 140 may estimate the thickness of each material included in the subject by performing the calculation defined in the following Equation 38.

$$[a_c - a_b \quad a_a - a_b]^+ [y - a_b T - b] = \qquad (38)$$

$$[I_2 \quad [a_c - a_b \quad a_a - a_b]^+ \quad c]\begin{bmatrix} t_c \\ t_a \\ t_c^2 \end{bmatrix}$$

In detail, in Equation 38, a thickness is estimated by calculating a pseudo inverse of $[a_c-a_b \ a_a-a_b]$ related to the first and second materials, which are assumed to be linear, from among columns included in an attenuation coefficient matrix, and then making a row including a quadratic equation about a material, which is obtained by approximating a query for estimating thicknesses of three materials to have a quadratic equation.

For example, when a nonlinear approximation is performed on the third material c, the thickness $t_c$ of the third material may be calculated by calculating a first row, and thicknesses $t_a$ and $t_b$ of the first and second materials may be calculated by calculating second and third rows by using calculated thickness $t_c$.

In addition, the thickness estimating unit 140 may estimate the thickness of each material included in the subject by performing the calculation defined in the following Equation 39.

$$\min_{t_c, t_f} \|y - b - a_b T - (a_c - a_b)t_c - (a_a - a_b)t_a - ct_c^2\|_2^2 \qquad (39)$$

In detail, in Equation 39, a cost function is calculated from Equation 37, and a value which makes the cost function to be minimum is calculated.

Thus, the thickness estimating unit 140 may estimate the thickness of each material included in the subject by using linear approximation or nonlinear approximation. In addition, the thicknesses of the materials may be correctly estimated by using optimal multi-energy radiation.

When a material has a small thickness of about 1 cm, the thickness of the material may be estimated by using linear approximation. However, when the thickness of the material is greater than about 1 cm, it is difficult to correctly estimate a thickness of the material by using linear approximation. In this case, the thickness estimating unit 140 may estimate a thickness of a material by using nonlinear approximation, as described above.

So far, a case where nonlinear approximation is performed on only a single material has been described. However, this example is not limited to this, and nonlinear approximation may also be performed on a plurality of materials, thereby further correctly estimating the thicknesses of the materials.

The probability estimating unit 150 estimates a probability that at least two materials included in the subject are distributed, by using the attenuation coefficient estimated by the attenuation-coefficient estimating unit 120. For example, the probability estimating unit 150 estimates the probability by using an F-test method. According to this example, the F-test method may include an F-contrast method.

The probability estimating unit 150 estimates a probability whether a pixel of a radiation image of the subject corresponds to a material from among at least two materials included in the subject. Thus, the radiation image of the subject may be qualitatively analyzed.

Hereinafter, a case where the probability estimating unit 150 estimates a probability by using the F-test method has been described, but this example is not limited thereto.

The F-test method according to this example may use an attenuation coefficient matrix as a dictionary, and may estimate a value indicating a unique characteristic about each row or combinations of rows of the attenuation coefficient matrix, in order to estimate a probability of materials included in the subject.

Thus, the probability estimating unit 150 may generate a probability map. The probability map may be generated by calculating a variation of residuals of all dictionary matrixes, calculating a variation of residuals of a reduced dictionary matrix, and thus matching a ratio of the calculated variations to an F-distribution. In this case, a variation may be calculated from a sum-of-squares of a residual.

The probability estimating unit 150 sets an attenuation coefficient matrix A estimated by the attenuation-coefficient estimating unit 120 as a dictionary matrix, and sets a contrast matrix C having a value only at some columns of the attenuation coefficient matrix A. Thus, the reduced dictionary matrix $A_C$ may be defined by the following Equation 40.

$$A_C = AC \qquad (40)$$

In Equation 40, $A_C$ is the reduced dictionary matrix including only a value of some columns of the dictionary matrix, A is the dictionary matrix, and C is a contrast matrix.

For example, when the reduced dictionary matrix $A_C$ is set so as to include only a value about a k-th column of the dictionary matrix A, elements of the contrast matrix C may be defined by the following Equation 41.

$$c_{ij} = \begin{cases} 1 & i=k, j=k \\ 0 & \text{otherwise} \end{cases} \quad (41)$$

Thus, when the dictionary matrix A is defined by the following Equation 42, the reduced dictionary matrix $A_C$ may be defined by the following Equation 43.

$$A = [a_1 a_1 \ldots a_K] \quad (42)$$

$$A_C = [0 \ldots 0 a_k 0 \ldots 0] \quad (43)$$

In addition, the remaining dictionary matrix $AP_C^\perp$ of the dictionary matrix A except for the reduced dictionary matrix $A_c$ may be defined by the following Equation 44 by projecting a column space or range space of the contrast matrix C to an orthogonal complement.

$$AP_C^\perp = A(I_K - CC^+) \quad (44)$$

In Equation 44, $P_C^\perp$ indicates a projection of a column space or range space of the contrast matrix C to an orthogonal complement, and $AP_C^\perp$ is the remaining dictionary matrix.

The residual of the reduced dictionary matrix $A_c$ may be obtained by removing a residual corresponding to the remaining dictionary matrix $AP_C^\perp$ from the entire residual. Thus, a residual forming matrix M of the reduced dictionary matrix $A_c$ may be calculated by a difference between a residual forming matrix $$P_{AP_C^\perp}^\perp$$

of the remaining dictionary matrix $AP_C^\perp$ and a residual forming matrix $P_A^\perp$ of an entire dictionary matrix A. Thus, a residual $r_C^\perp$ of the reduced dictionary matrix $A_c$ may be defined by the following Equation 45.

$$\begin{aligned} r_C^\perp &= My \quad (45) \\ &= (P_{AP_C^\perp}^\perp - P_A^\perp)y \\ &= ((I_M - AP_C^\perp(AP_C^\perp)^+) - (I_M - AA^+))y \end{aligned}$$

In Equation 45, M is a residual forming matrix of the reduced dictionary matrix $A_c$, y is a measurement value matrix obtained by passing multi-energy radiation through the subject, $$P_{AP_C^\perp}^\perp$$

is a residual forming matrix of the remaining dictionary matrix $AP_C^\perp$, and $P_A^\perp$ is a residual forming matrix of the entire dictionary matrix A.

Thus, the probability estimating unit 150 calculates variations of residuals $P_A^\perp y$ of the entire dictionary matrix A and residuals My of the reduced dictionary matrix $A_c$, respectively, by using a sum-of-squares. Thus, as defined in the following Equation 46, a ratio of the variations may follow an F-distribution.

$$F = \frac{(My)^T MY}{(P_A^\perp y)^T P_A^\perp y} \frac{R-p}{p_1} \sim F_{P_1, R-p} \quad (46)$$

In Equation 46, My is a residual of the reduced dictionary matrix $A_c$, $P_A^\perp y$ is a residual of the entire dictionary matrix A, R is a dimension of the measurement value matrix y, p is rank(A), and $p_1$ is rank(M).

The probability estimating unit 150 may calculate a p-value including information indicating whether each pixel included in a radiation image corresponds to each of at least two materials included in the subject, based on the F-distribution defined in Equation 46. In this case, the p-value has 0 or more, or 1 or less. The closer the p-value is to 0, the more meaningful the p-value is.

For example, with respect to any one pixel from among a plurality of pixels included in a radiation image of the subject including the first through third materials, the probability estimating unit 150 estimates a first p-value corresponding to the first material, a second p-value corresponding to the second material, and a third p-value corresponding to the third material Thus, the probability estimating unit 150 may estimate probabilities that pixels correspond to the first through third materials, respectively, with reference to the calculated first through third p-values. In this case, the closer the first p-value is to 0, the smaller a probability that a pixel corresponds to the first material when the pixel does not correspond to the first material, which is also applicable to the second p-value and the third p-value.

Thus, the probability estimating unit 150 may estimate probabilities that each pixel included in a radiation image corresponds to the first through third materials, respectively.

The diagnosis image generating unit 160 generates a diagnosis image of the subject.

For example, the diagnosis image generating unit 160 may generate the diagnosis image where a material corresponding to a region of interest is separated, by using the thickness estimated by the thickness estimating unit 140. In this case, the region of interest is a region about which a user is concerned and which is to be observed by the user. The region of interest may indicate a region including a tissue that is likely to correspond to a lesion. For example, the lesion may be a microcalcification, carcinoma tissue, or the like.

As another example, the diagnosis image generating unit 160 may generate a diagnosis image showing a probability that each pixel included in the diagnosis image corresponds to one of the at least two materials included in the subject by using the probability estimated by the probability estimating unit 150.

In this case, the diagnosis image showing a probability that each pixel included in the diagnosis image corresponds to one of the at least two materials included in the subject may show colors corresponding to tissues corresponding to respective pixels, by using a plurality of colors respectively corresponding to the at least two materials. In this case, the higher a distribution probability, the darker a color. For example, if the at least two materials include adipose tissue and carcinoma tissue, pixels corresponding to the adipose tissue may be displayed in gray, and pixels corresponding to the carcinoma tissue may be displayed in red. However, these are merely examples, and this example is not limited to this.

Thus, since the diagnosis image of the subject indicates a shape of distributing tissues included in the subject, diagnosis may be further correctly performed by using the diagnosis image captured by the radiation image capturing apparatus 100.

The display unit 170 displays the diagnosis image generated by the diagnosis image generating unit 160. The display unit 170 includes an output device such as a display panel, a touch screen, a liquid crystal display (LCD) display, or a monitor, and software for driving the output device, which are included in the radiation image capturing apparatus 100.

Thus, the radiation image capturing apparatus 100 may display the diagnosis image in which a material, as a region of interest, from among materials included in the subject is separated, or may display the diagnosis image having a probability that each pixel included in the diagnosis image corresponds to the respective tissues included in the subject. Thus, a user may intuitively recognize whether the subject contains a lesion, by using the radiation image capturing apparatus 100.

Figure 3:
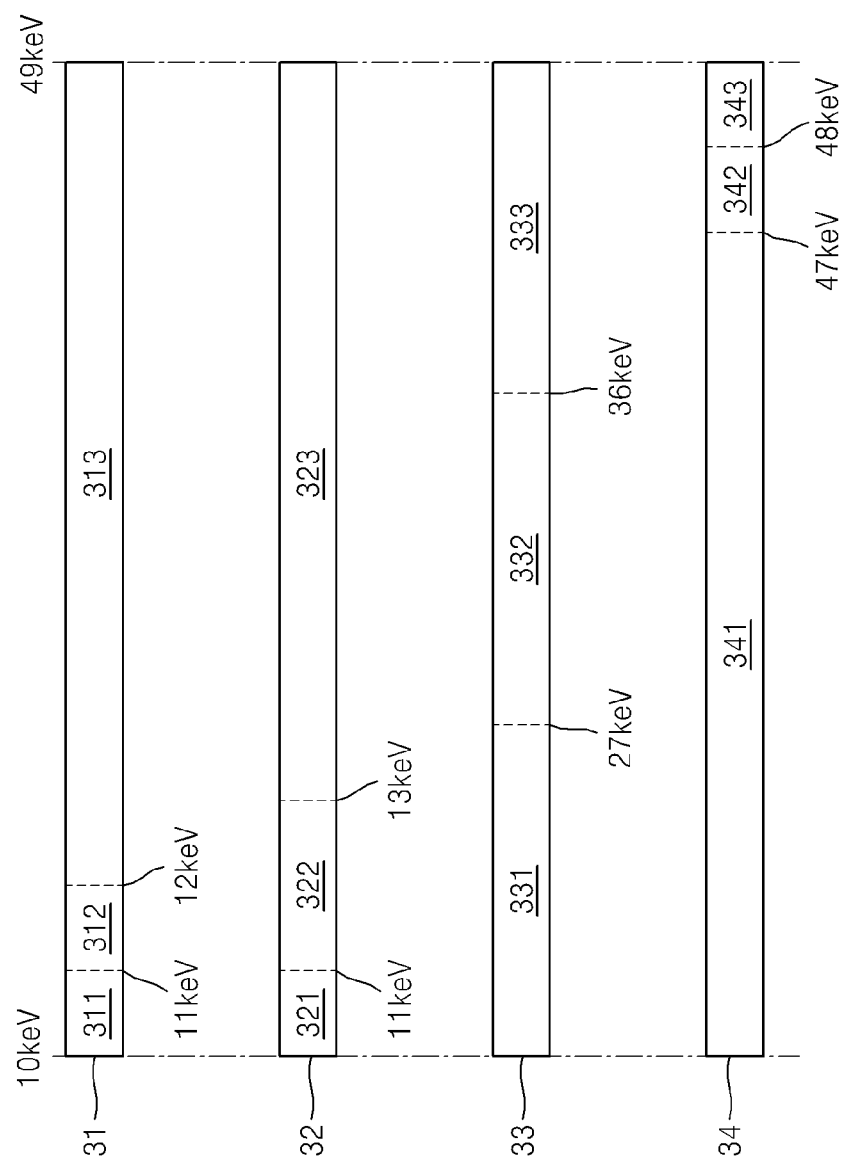
FIG. 3 shows a plurality of multi-energy radiations having different combinations of at least two energy bands according to an example of the invention.

FIG. 3 shows a plurality of multi-energy radiations having different combinations of at least two energy bands according to an example of the invention.

Referring to FIGS. 2 and 3, the energy-band setting unit 105 sets boundaries for dividing an energy band corresponding to radiation into at least two energy bands, and sets a plurality of multi-energy radiations having different combinations of at least two energy bands included in the multi-energy radiations.

When an energy band corresponding to radiation is 10 keV or more, or 49 keV or less, a case where multi-energy radiation includes combinations of three energy bands will be described.

The energy-band setting unit 105 may set 11 keV and 12 keV as boundaries and may set a first multi-energy radiation 31. A range of a first energy band 311 included in the first multi-energy radiation 31 may be 10 keV or more, or 11 keV or less. A range of a second energy band 312 included in the first multi-energy radiation 31 may be 11 keV or more, or 12 keV or less. A range of a third energy band 313 included in the first multi-energy radiation 31 may be 12 keV or more, or 49 keV or less.

In addition, the energy-band setting unit 105 may set 11 keV and 13 keV as boundaries, and may set a second multi-energy radiation 32. A range of a first energy band 321 included in the second multi-energy radiation 32 may be 10 keV or more, or 11 keV or less. A range of a second energy band 322 included in the second multi-energy radiation 32 may be 11 keV or more, or 13 keV or less. A range of a third energy band 323 included in the second multi-energy radiation 32 may be 13 keV or more, or 49 keV or less.

In addition, the energy-band setting unit 105 may set 27 keV and 36 keV as boundaries, and may set a third multi-energy radiation 33. A range of a first energy band 331 included in the third multi-energy radiation 33 may be 10 keV or more, or 27 keV or less. A range of a second energy band 332 included in the third multi-energy radiation 33 may be 27 keV or more, or 36 keV or less. A range of a third energy band 333 included in the third multi-energy radiation 33 may be 36 keV or more, or 49 keV or less.

In addition, the energy-band setting unit 105 may set 47 keV and 48 keV as boundaries, and may set a fourth multi-energy radiation 34. A range of a first energy band 341 included in the fourth multi-energy radiation 34 may be 10 keV or more, or 47 keV or less. A range of a second energy band 342 included in the fourth multi-energy radiation 34 may be 47 keV or more, or 48 keV or less. A range of a third energy band 343 included in the fourth multi-energy radiation 34 may be 48 keV or more, or 49 keV or less.

As described above, the energy-band setting unit 105 may set a plurality of multi-energy radiations based on various combinations as boundaries for dividing an energy band of radiation by 1 keV.

Figure 4:
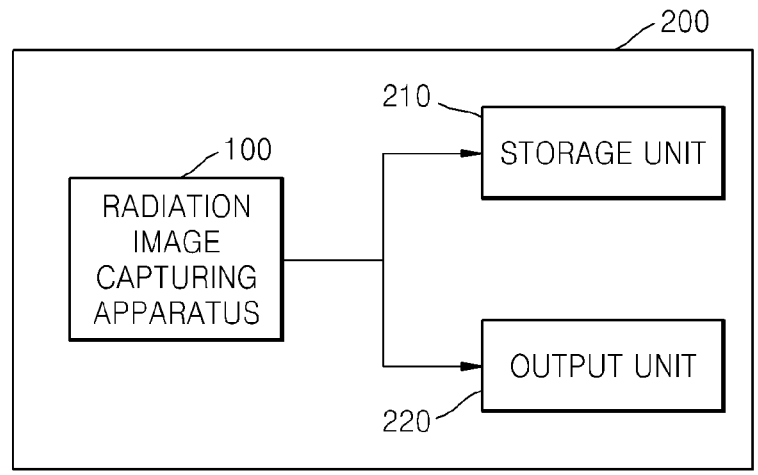
FIG. 4 is a block diagram of a medical imaging system according to an example of the invention.

FIG. 4 is a block diagram of a medical imaging system 200 according to an example of the invention. The medical imaging system 200 includes the radiation image capturing apparatus 100, a storage unit 210, and an output unit 220.

Elements related to this example are illustrated in FIG. 4. However, it will be understood by those skilled in the art that besides the elements illustrated in FIG. 4 other general elements may be further included.

The radiation image capturing apparatus 100 of FIG. 4 may correspond to an example of the radiation image capturing apparatus 100 shown in FIGS. 1 and 2. Thus, the detailed description of the radiation image capturing apparatus 100 of FIGS. 1 and 2 is also applicable to the radiation image capturing apparatus 100 of FIG. 4, and thus is not repeated herein.

The radiation image capturing apparatus 100 of FIG. 4 irradiates multi-energy radiation having at least two energy bands to the calibration means that is formed of at least two materials with each of at least two materials having a plurality of thicknesses, estimates an attenuation coefficient by using a value obtained by passing multi-energy radiation through the calibration means, determines an optimal combination from among combinations of at least two energy bands to be included in multi-energy radiation, with reference to the estimated attenuation coefficient and the value obtained by passing multi-energy radiation through the calibration means, and generates a diagnosis image of the subject by irradiating multi-energy radiation based on the determined combination.

The storage unit 210 stores the diagnosis image generated by the radiation image capturing apparatus 100 and data generated during an operation of the medical imaging system 200.

For instance, the storage unit 210 is a general storage medium. It will be understood by those skilled in the art that the storage unit 210 may include a Hard Disk Drive (HDD), a Read Only Memory (RAM), a Random Access Memory (RAM), a flash memory, a memory card, or any other type of storage medium known in the art that is capable of storing the diagnosis image generated by the radiation image capturing apparatus 100 and the data generated during the operation of the medical imaging system 200.

The output unit 220 may transmit/receive data to/from the external device through a wired or wireless network or wired series communication. For example, the output unit 220 may output the diagnosis image generated by the radiation image capturing apparatus 100 to the external device through a network. Examples of such a network include the Internet, a Local Area Network (LAN), a Wireless LAN, Wide Area Network (WAN), a Personal Area Network (PAN), and the like. However, this example is not limited to this, and the network may be any other kind of network for transmitting and receiving information.

The external device may be another medical image system located at another place, a general computer system, a fax machine, or the like.

It will be also understood by those skilled in the art that the storage unit 210 and the output unit 220 according to this example may further include image interpretation and search functions to be integrated into one system, such as a Picture Archiving and Communication System (PACS).

Figure 5:
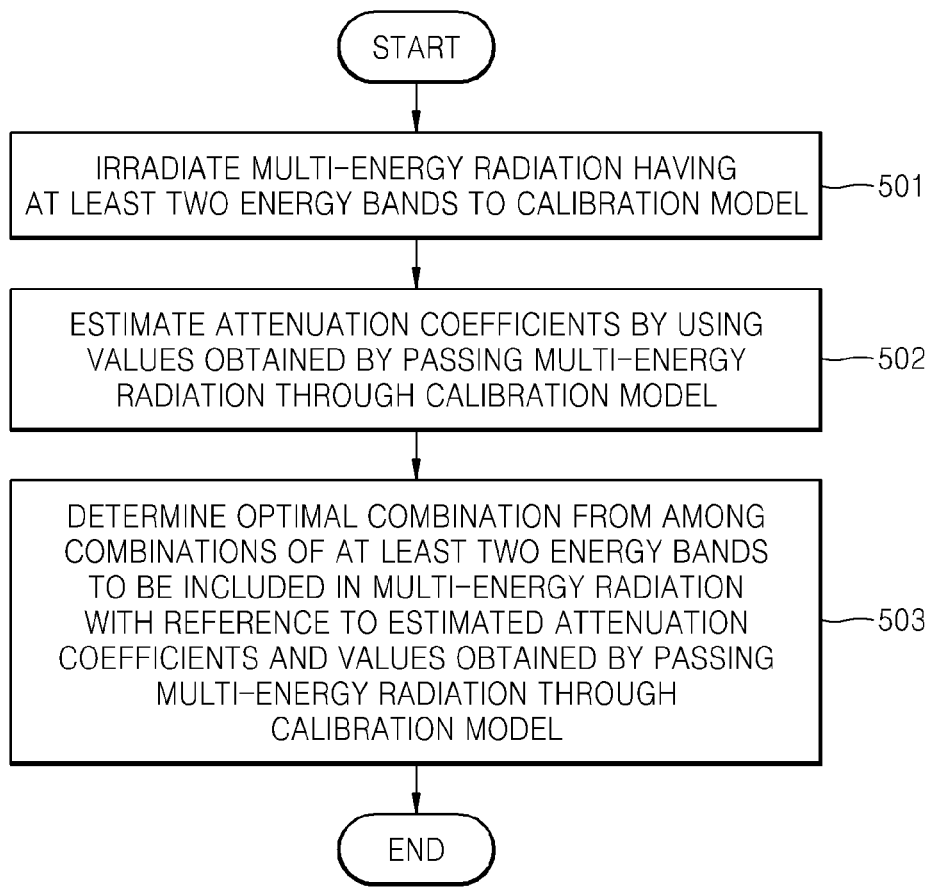
FIG. 5 is a flowchart of a method of determining an optimal energy band of multi-energy radiation according to an example of the invention.

FIG. 5 is a flowchart of a method of determining an optimal energy band of multi-energy radiation according to an example of the invention. Referring to FIG. 5, the method of determining an optimal energy band of multi-energy radiation includes operations that are performed by the radiation image capturing apparatus 100 or the medical imaging system 200 of FIGS. 1, 2 and 4 in a time sequence. Thus, although omitted below, the detailed description of the radiation image capturing apparatus 100 or the medical imaging system 200 of FIGS. 1, 2 and 4 is also applicable to the method of determining an optimal energy band of multi-energy radiation of FIG. 5.

In operation 501, the radiation irradiation unit 110 irradiates multi-energy radiation having at least two energy bands to a calibration means that is formed of at least two materials with each of at least two materials having a plurality of thicknesses.

In operation 502, the attenuation-coefficient estimating unit 120 estimates attenuation coefficients of each of the at least two materials with respect to each of the at least two energy bands by using values obtained by passing the multi-energy radiation through the calibration means.

In operation 503, the energy-band determining unit 130 determines an optimal combination from among combinations of at least two energy bands to be included in multi-energy radiation, with reference to the estimated attenuation coefficients and the values obtained by passing the multi-energy radiation through the calibration means.

Thus, multi-energy radiation based on an optimal combination may be determined, and thus a radiation image of the subject may be captured by using the determined multi-energy radiation.

Figure 6:
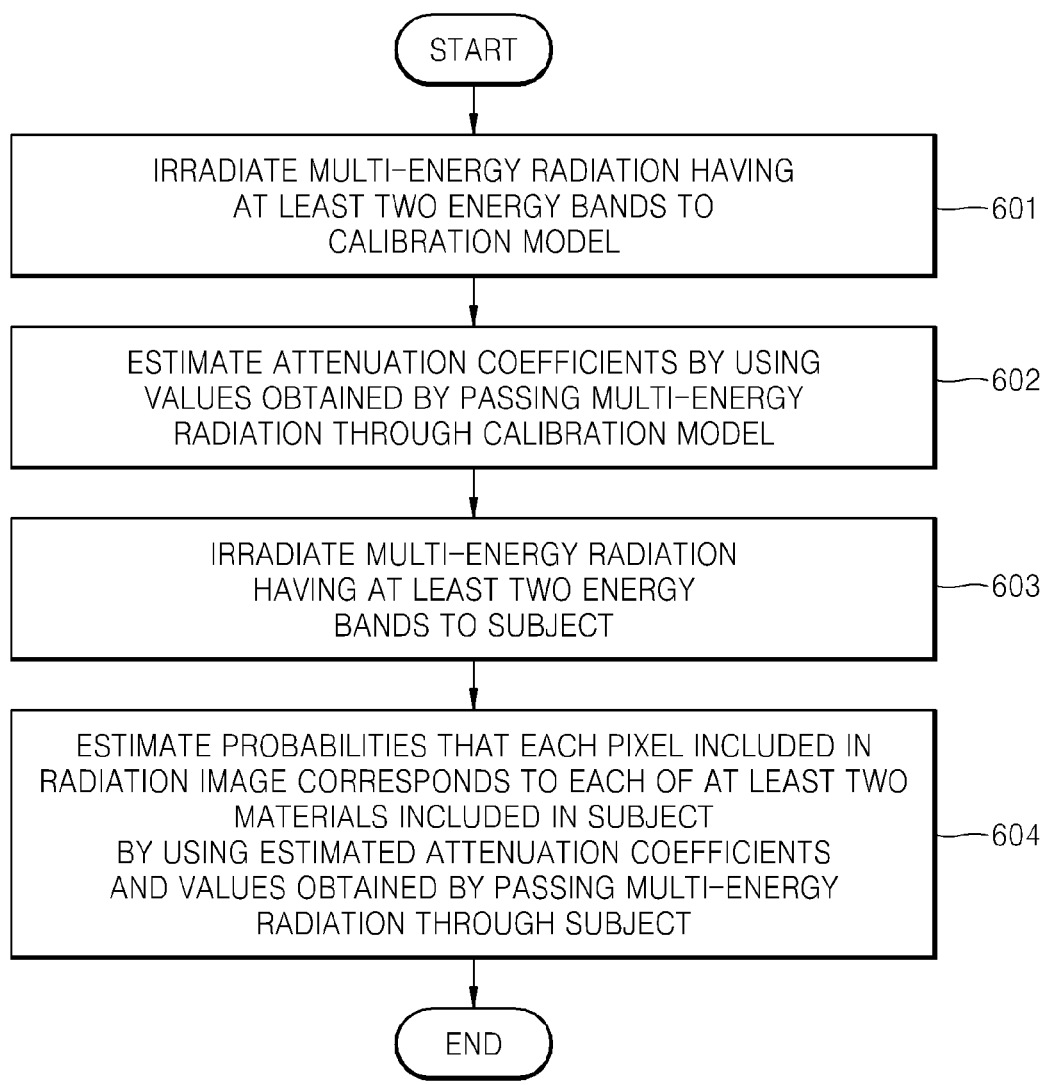
FIG. 6 is a flowchart of a method of processing a radiation image of a subject according to an example of the invention.

FIG. 6 is a flowchart of a method of processing a radiation image of a subject according to an example of the invention. Referring to FIG. 6, the method of processing a radiation image includes operations that are performed by the radiation image capturing apparatus 100 or the medical imaging system 200 of FIGS. 1, 2 and 4 in a time sequence. Thus, although omitted below, the detailed description of the radiation image capturing apparatus 100 or the medical imaging system 200 of FIGS. 1, 2 and 4 is also applicable to the method of processing a radiation image of FIG. 6.

In operation 601, the radiation irradiation unit 110 irradiates multi-energy radiation having at least two energy bands to the calibration means that is formed of at least two materials with each of at least two materials having a plurality of thicknesses.

In operation 602, the attenuation-coefficient estimating unit 120 estimates attenuation coefficients of each of the at least two materials for each of the at least two energy bands by using values obtained by passing the multi-energy radiation through the calibration means.

In operation 604, the radiation irradiation unit 110 irradiates the multi-energy radiation having at least two energy bands to the subject.

In operation 604, the probability estimating unit 150 estimates probabilities that each pixel included in a radiation image corresponds to each of at least two materials included in the by using the estimated attenuation coefficients and the values obtained by passing the multi-energy radiation through the subject.

Thus, since pixels included in a radiation image indicate probabilities that each pixel included in a radiation image corresponds to each of at least two materials included in the subject, whether the subject contains a lesion may be intuitively recognized.

Figure 7:
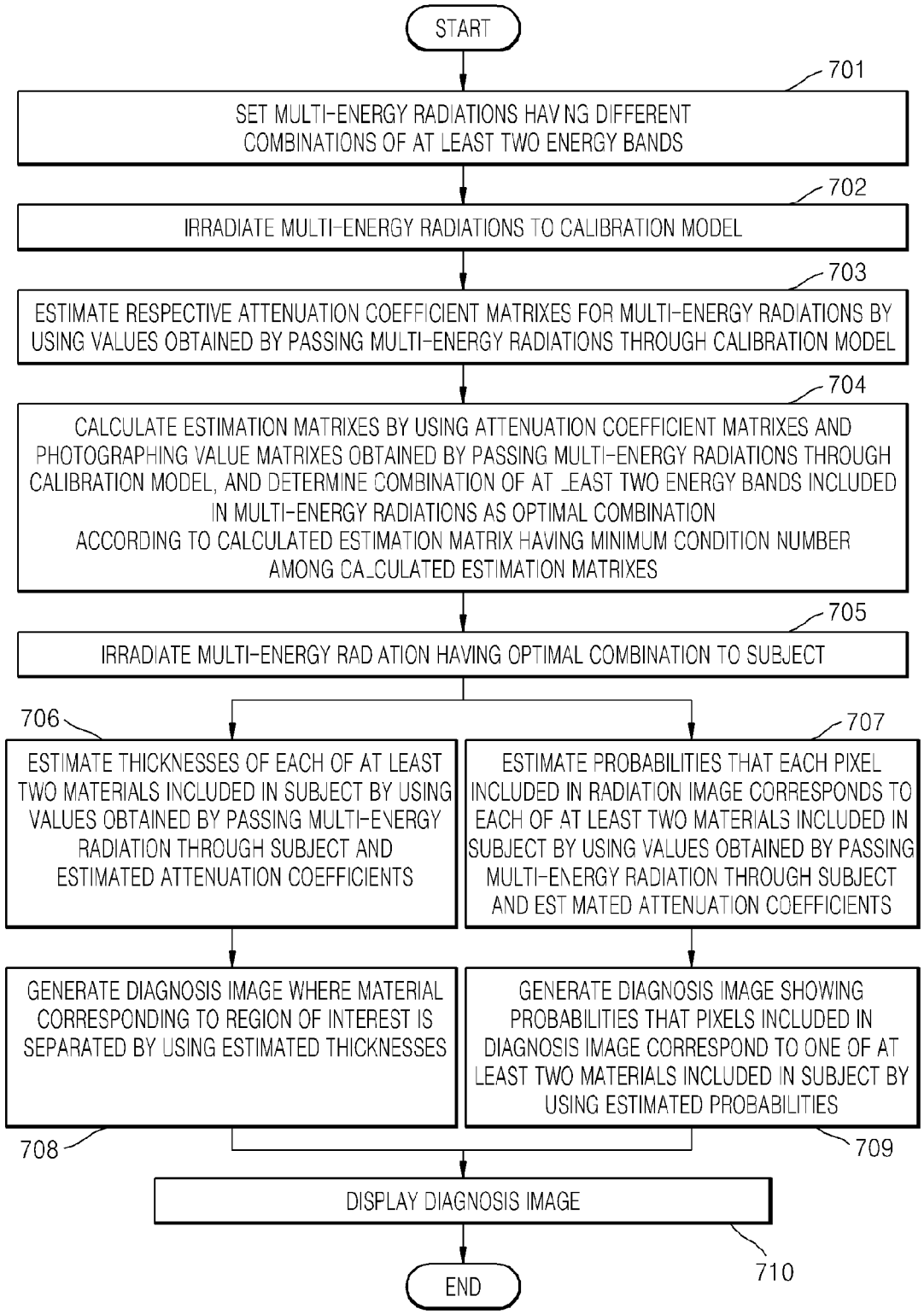
FIG. 7 is a flowchart of a method of capturing a radiation image of a subject according to an example of the invention.

FIG. 7 is a flowchart of a method of capturing a radiation image of a subject according to an example of the invention. Referring to FIG. 7 the method of capturing a radiation image of a subject may includes operations that are performed by the radiation image capturing apparatus 100 or the medical imaging system 200 of FIGS. 1, 2 and 4 in a time sequence. Thus, although omitted below, the detailed description of the radiation image capturing apparatus 100 or the medical imaging system 200 of FIGS. 1, 2 and 4 is also applicable to the method of capturing a radiation image of a subject of FIG. 7.

In operation 701, the energy-band setting unit 105 sets boundaries for dividing an energy band of radiation into at least two energy bands, and sets a plurality of multi-energy radiations having different combinations of at least two energy bands.

In operation 702, the radiation irradiation unit 110 irradiates the multi-energy radiations set in operation 701 to the calibration means having at least two materials with each of at least two materials having a plurality of thicknesses.

In operation 703, the attenuation-coefficient estimating unit 120 estimates respective attenuation coefficient matrixes for the multi-energy radiations by using the values obtained by passing the multi-energy radiations through the calibration means.

In operation 704, the energy-band determining unit 130 calculates estimation matrixes by using the attenuation coefficient matrixes and photographing value matrixes obtained by passing the multi-energy radiations through the calibration means, and determines a combination of at least two energy bands included in the multi-energy radiations as an optimal combination of at least two energy bands according to a calculated estimation matrix having a minimum condition number among the calculated estimation matrixes.

For example, the energy-band setting unit 105 sets first through fifth multi-energy radiations, and the radiation irradiation unit 110 irradiates each of the first through fifth multi-energy radiations to the calibration means. The attenuation-coefficient estimating unit 120 estimates first through fifth attenuation coefficient matrixes respectively corresponding to the first through fifth multi-energy radiations. In addition, the attenuation-coefficient estimating unit 120 obtains first through fifth photographing value matrixes by passing the first through fifth multi-energy radiations through the calibration means.

Thus, the energy-band determining unit 130 calculates a first estimation matrix by using a first attenuation coefficient matrix and a first photographing value matrix, and similarly, calculates second through fifth estimation matrixes using second through fifth attenuation coefficient matrixes and second through fifth photographing value matrixes. In addition, the energy-band determining unit 130 calculates condition numbers of the first through fifth estimation matrixes, and determines a combination of at least two energy bands included in the multi-energy radiations as an optimal combination of at least two energy bands according to a calculated estimation matrix having a minimum condition number among the first through fifth calculates estimation matrixes.

For example, when a condition number of the third calculated estimation matrix is a minimum condition number, the energy-band determining unit 130 determines a combination of at least two energy bands included in the third multi-energy radiation as an optimal combination of at least two energy bands.

In operation 705, the radiation irradiation unit 110 irradiates the multi-energy radiation having the optimal combination at least two energy bands determined in operation 704 to the subject.

In operation 706, the thickness estimating unit 140 estimates thicknesses of each of at least two materials included in the subject by using values obtained by passing the multi-energy radiation of operation 705 through the subject and the attenuation coefficients estimated in operation 703.

In operation 707, the probability estimating unit 150 estimates probabilities that each pixel included in a radiation image corresponds to each of at least two materials included in the subject by using the values obtained by passing the multi-energy radiation of operation 705 through the subject and the attenuation coefficients estimated in operation 703.

In operation 708, the diagnosis image generating unit 160 generates a diagnosis image where a material corresponding to a region of interest is separated by using the thicknesses estimated in operation 706.

In operation 709, the diagnosis image generating unit 160 generates a diagnosis image showing probabilities that pixels included in the diagnosis image correspond to one of the at least two materials included in the subject by using the probabilities estimated in operation 707.

In operation 710, the display unit 170 displays the diagnosis image generated in operation 708 and/or the diagnosis image generated in operation 709.

Accordingly, a diagnosis image of a material corresponding to a region of interest from among a plurality of materials included in the subject, or a diagnosis image showing probabilities of pixels corresponding to a plurality of materials included in the subject, may be displayed, and thus a correctness of a diagnosis may be improved by using the diagnosis images.

Since the radiation image capturing apparatus 100 determines an optimal energy band of multi-energy radiation for capturing a radiation image, the image quality of a diagnosis image may be improved by using the optimal energy band. In addition, the optimal energy band is determined by using a calibration means, and thus the subject may be prevented from being excessively exposed to radiation.

In addition, the radiation image capturing apparatus 100 may generate a diagnosis image corresponding to a region of interest by estimating thicknesses of materials included in the subject, or may generate a diagnosis image showing probabilities of pixels corresponding to a plurality of materials included in the subject, and thus a user may definitely perform a quantitative analysis or a qualitative analysis.

The energy-band setting unit 105, the attenuation-coefficient estimating unit 120, the energy-band determining unit 130, the thickness estimating unit 140, the probability estimating unit 150, and the diagnosis image generating unit 160 in FIGS. 1 and 2, which may be included in the radiation image capturing apparatus 100 in FIG. 4, may be implemented using hardware components and/or software components. Software components may be implemented by a processing device, which may be implemented using one or more general-purpose or special-purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purposes of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such a parallel processors.

As used herein, a processing device configured to implement a function A includes a processor programmed to run specific software. In addition, a processing device configured to implement a function A, a function B, and a function C may include configurations, such as, for example, a processor configured to implement functions A, B, and C; a first processor configured to implement function A and a second processor configured to implement functions B and C; a first processor configured to implement functions A and B and a second processor configured to implement function C; a first processor to implement function A, a second processor configured to implement function B, and a third processor configured to implement function C; a first processor configured to implement functions A, B, C and a second processor configured to implement functions A, B, and C, and so on.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion.

In particular, the software and data may be stored by one or more non-transitory computer-readable storage mediums. The non-transitory computer-readable storage medium may include any data storage device that can store data that can be thereafter read by a computer system or processing device. Examples of a non-transitory computer-readable storage medium include read-only memory (ROM), random-access memory (RAM), CD-ROMs, magnetic tapes, floppy disks, and optical data storage devices. Also, functional programs, codes, and code segments for implementing the examples disclosed herein can be easily, constructed by programmers skilled in the art to which the examples pertain based on the drawings and their corresponding descriptions as provided herein.

While this disclosure has been particularly shown and described with reference to examples thereof, it will be understood by those skilled in the art that various changes in form and details may be made in these examples without departing from the spirit and scope of the invention as defined by the claims and their equivalents. It should be understood that the examples described herein should be considered in a descriptive sense only, and not for purposes of limitation. Descriptions of features or aspects in each example are to be considered as being applicable to similar features or aspects in other examples. Suitable results may be achieved if the described techniques are performed in a different order and/or if components in a described system, architecture, device, or circuit are combined in a different manner and/or replaced or supplemented by other components or their equivalents. Therefore, the scope of the invention is defined not by the detailed description of the disclosure, but by the claims and their equivalents, and all variations within the scope of the claims and their equivalents are to be construed as being included in the invention.

What is claimed is:

1. An apparatus for capturing a radiation image of a subject, the subject comprising at least two materials, the apparatus comprising:

a radiation irradiating unit configured to irradiate multi-energy radiation comprising at least two energy bands to a calibration model comprising a plurality of thicknesses of each of the at least two materials;
an attenuation-coefficient estimating unit configured to estimate attenuation coefficients for each of the at least two materials for each of the at least two energy bands based on values obtained by passing the multi-energy radiation through the calibration model; and
an energy-band determining unit configured to determine an optimal combination of at least two energy bands to be included in multi-energy radiation to be irradiated to the subject from a plurality of different combinations of at least two energy bands based on the attenuation coefficients estimated by the attenuation-coefficient estimating unit and the values obtained by passing the multi-energy radiation through the calibration model.

2. The apparatus of claim 1, wherein the energy-band determining unit is further configured to determine the optimal combination of at least two energy bands to be included in the multi-energy radiation to be irradiated to the subject based on a condition number calculated based on an attenuation coefficient matrix and a photographing value matrix;
the attenuation coefficient matrix comprises the attenuation coefficients for each of the at least two materials for each of the at least two energy bands; and
the photographing value matrix comprises the values obtained by passing the multi-energy radiation through the calibration model.

3. The apparatus of claim 2, wherein the energy-band determining unit is further configured to calculate the condition number based on a ratio of a maximum singular value and a minimum singular value of an estimation matrix calculated based on the attenuation coefficient matrix and the photographing value matrix.

4. The apparatus of claim 1, further comprising an energy-band setting unit configured to:
set boundaries for dividing an energy band of radiation into at least two energy bands; and
set a plurality of multi-energy radiations each comprising a different one of the plurality of different combinations of at least two energy bands by setting different boundaries for each of the plurality of multi-energy radiations.

5. The apparatus of claim 4, wherein the radiation irradiating unit is further configured to irradiate the plurality of multi-energy radiations to the calibration model;
the attenuation-coefficient estimating unit is further configured to estimate respective attenuation coefficient matrixes for the plurality of multi-energy radiations based on values obtained by passing the multi-energy radiations through the calibration model; and
the energy-band determining unit is further configured to:
calculate estimation matrixes based on the attenuation coefficient matrixes and respective photographing value matrixes obtained by passing the multi-energy radiations through the calibration model; and
determine a combination of at least two energy bands included in one of the multi-energy radiations as the optimal combination of at least two energy bands to be included in the multi-energy radiation to be irradiated to the subject based on a calculated estimation matrix having a minimum condition number among the calculated estimation matrixes.

6. The apparatus of claim 1, further comprising a thickness estimating unit configured to estimate thicknesses of each of the at least two materials of the subject based on the attenuation coefficients and values obtained by passing the multi-energy radiation comprising the optimal combination of at least two energy bands through the subject.

7. The apparatus of claim 1, further comprising a probability estimating unit configured to estimate probabilities that each pixel of the radiation image corresponds to each of the at least two materials of the subject based on the attenuation coefficients and values obtained by passing the multi-energy radiation comprising the optimal combination of at least two energy bands through the subject.

8. The apparatus of claim 7, wherein the probability estimating unit is further configured to estimate the probabilities using an F-test method.

9. The apparatus of claim 7, further comprising a diagnosis image generating unit configured to generate a diagnosis image showing probabilities that each pixel of the diagnosis image corresponds to one of the at least two materials of the subject based on the estimated probabilities.

10. The apparatus of claim 9, further comprising a display unit for configured to display the diagnosis image.

11. The apparatus of claim 1, wherein the calibration model comprises:
a plurality of calibration phantoms each comprising a different one of the plurality of thicknesses of a different one of the at least two materials; or
a plurality of calibration phantoms each comprising the plurality of thicknesses of a different one of the at least two materials; or
a single calibration phantom comprising the plurality of thicknesses of each of the at least two materials.

12. A medical imaging system comprising:
a radiation image capturing apparatus for capturing a radiation image of a subject, the subject comprising at least two materials, the radiation image capturing apparatus being configured to:
irradiate multi-energy radiation comprising at least two energy bands to a calibration model comprising a plurality of thicknesses of each of the at least two materials;
estimate attenuation coefficients for each of the at least two materials for each of the at least two energy bands based on values obtained by passing the multi-energy radiation through the calibration model;
determine an optimal combination of at least two energy bands to be included in multi-energy radiation to be irradiated to the subject from a plurality of different combinations of at least two energy bands based on the attenuation coefficients and the values obtained by passing the multi-energy radiation through the calibration model; and
generate a diagnosis image of the subject by irradiating the multi-energy radiation comprising the optimal combination of at least two energy bands to the subject;
a storage unit configure to store the diagnosis image; and
an output unit configured to output the diagnosis image to an external device.

13. The medical imaging system of claim 12, wherein the radiation image capturing apparatus is further configured to estimate probabilities that each pixel of the radiation image corresponds to each of the at least two materials of the subject based on the attenuation coefficients and values obtained by passing the multi-energy radiation comprising the optimal combination of at least two energy bands through the subject.

14. A method of determining an optimal combination of at least two energy bands to be included in multi-energy radiation to be irradiated to a subject for capturing a radiation image of the subject, the subject comprising at least two materials, the method comprising:
irradiating multi-energy radiation comprising at least two energy bands to a calibration model comprising a plurality of thicknesses of the at least two materials;

estimating attenuation coefficients for each of the at least two materials for each of the at least two energy bands based on values obtained by passing the multi-energy radiation through the calibration model; and determining the optimal combination of at least two energy bands to be included in the multi-energy radiation to be irradiated to the subject from a plurality of different combinations of at least two energy bands based on the attenuation coefficients and the values obtained by passing the multi-energy radiation through the calibration model.

15. The method of claim 14, wherein the determining comprises determining the optimal combination of at least two energy bands to be included in the multi-energy radiation to be irradiated to the subject based on a condition number calculated based on an attenuation coefficient matrix and a photographing value matrix;

the attenuation coefficient matrix comprises the attenuation coefficients for each of the at least two materials for each of the at least two energy bands; and the photographing value matrix comprises the values obtained by passing the multi-energy radiation through the calibration model.

16. The method of claim 14, further comprising setting a plurality of multi-energy radiations each comprising a different one of the plurality of different combinations of at least two energy bands by setting different boundaries for dividing an energy band of radiation into at least two energy bands for each of the plurality of multi-energy radiations.

17. The method of claim 16, further comprising:
irradiating the plurality of multi-energy radiations to the calibration model;
estimating respective attenuation coefficient matrixes for the plurality of multi-energy radiations based on values obtained by passing the multi-energy radiations through the calibration model;
calculating estimation matrixes based on the attenuation coefficient matrixes and respective photographing value matrixes obtained by passing the multi-energy radiations through the calibration models; and
determining a combination of at least two energy bands included in one of the multi-energy radiations as the optimal combination of at least two energy bands to be included in the multi-energy radiation to be irradiated to the subject based on a calculated estimation matrix having a minimum condition number from the calculated estimation matrixes.

18. The method of claim 14, further comprising:
irradiating the multi-energy radiation comprising the optimal combination of at least two energy bands to the subject; and
estimating probabilities that each pixel of the radiation image corresponds to each of the at least two materials of the subject based on the attenuation coefficients and values obtained by passing the multi-energy radiation comprising the optimal combination of at least two energy bands through the subject.

19. A non-transitory computer-readable storage medium storing a program for controlling a processor to perform the method of claim 14.

20. A method of processing a radiation image of a subject, the subject comprising at least two materials, the method comprising:
irradiating multi-energy radiation comprising at least two energy bands to a calibration model comprising a plurality of thicknesses of each of the at least two materials;

estimating attenuation coefficients for each of the at least two materials for each of the at least two energy bands based on values obtained by passing the multi-energy radiation through the calibration model;
irradiating the multi-energy radiation to the subject; and
estimating probabilities that each pixel of the radiation image corresponds to each of the at least two materials of the subject based on the attenuation coefficients and values obtained by passing the multi-energy radiation through the subject.

21. A non-transitory computer-readable storage medium storing a program for controlling a processor to perform the method of claim 20.

22. An apparatus for capturing a radiation image of a subject, the subject comprising at least two materials, the apparatus comprising:
an energy-band setting unit configured to:
set a plurality of different combinations of at least two energy bands; and
set a plurality of multi-energy radiations each comprising a different one of the plurality of different combinations of at least two energy bands;
a radiation irradiating unit configured to:
sequentially irradiate the plurality of multi-energy radiations to a calibration model comprising a plurality of thicknesses of each of the at least two materials of the subject so that the plurality of multi-energy radiations sequentially pass through the calibration model in a calibration operation; and
irradiate a multi-energy radiation comprising an optimal combination of at least two energy bands to the subject so that the multi-energy radiation comprising the optimal combination of at least two energy bands passes through the subject in an imaging operation;
an attenuation-coefficient estimating unit configured to:
acquire calibration measurement values of each of the plurality of multi-energy radiations after each of the multi-energy radiations has passed through the calibration model; and
estimate attenuation coefficients for each of the at least two materials for each of the at least two energy bands of each of the plurality of multi-energy radiations based on the calibration measurement values;
an energy-band determining unit configured to determine the optimal combination of at least two energy bands of the multi-energy radiation to be irradiated to the subject from the plurality of different combinations of at least two energy bands of the plurality of multi-energy radiations based on the estimated attenuation coefficients and the calibration measurement values;
an image value estimating unit configured to:
acquire image measurement values of the multi-energy radiation comprising the optimal combination of at least two energy bands after the multi-energy radiation comprising the optimal combination of at least two energy bands has passed through the subject; and
estimate image values indicative of the subject based on optimal estimated attenuation coefficients that correspond to the optimal combination of at least two energy bands among the estimated attenuation coefficients estimated by the attenuation-coefficient estimating unit and the image measurement values; and
a diagnosis image generating unit configured to generate a diagnosis image of the subject based on the image values.

23. The apparatus of claim 22, wherein the image value estimating unit comprises a thickness estimating unit configured to estimate, as the image values, thicknesses of each of the at least two materials of the subject based on the estimated optimal attenuation coefficients and the image measurement values; and the diagnosis image generating unit is further configured to generate a diagnosis image of one of the at least two materials of the subject based on the estimated thicknesses.

24. The apparatus of claim 22, wherein the image value estimating unit comprises a probability estimating unit configured to estimate, as the image values, probabilities that each pixel of the radiation image corresponds to each of the at least two materials of the subject based on the estimated optimal attenuation coefficients and the image measurement values; and the diagnosis image generating unit is further configured to generate a diagnosis image comprising a plurality of pixels showing probabilities that each of the pixels corresponds to one of the at least two materials of the subject.

* * * * *